(12) United States Patent
Bergmann et al.

(10) Patent No.: US 11,548,911 B2
(45) Date of Patent: Jan. 10, 2023

(54) CLEAVABLE LINKER FOR PEPTIDE SYNTHESIS

(71) Applicant: ROCHE SEQUENCING SOLUTIONS, INC., Pleasanton, CA (US)

(72) Inventors: Frank Bergmann, Iffeldorf (DE); Simon Ferdinand Loibl, Wolfratshausen (DE); Sebastian Johannes Pomplun, Cambridge, MA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 17/170,060

(22) Filed: Feb. 8, 2021

(65) Prior Publication Data

US 2021/0155654 A1     May 27, 2021

Related U.S. Application Data

(63) Continuation of application No. PCT/EP2019/071161, filed on Aug. 7, 2019.

(30) Foreign Application Priority Data

Aug. 9, 2018 (EP) ..................................... 18188135

(51) Int. Cl.
    *C07K 1/04*        (2006.01)
    *C07C 271/22*    (2006.01)
    *C07K 14/00*     (2006.01)

(52) U.S. Cl.
    CPC .............. *C07K 1/04* (2013.01); *C07C 271/22* (2013.01); *C07K 14/001* (2013.01)

(58) Field of Classification Search
    CPC ........ C07K 1/04; C07K 14/001; C07C 271/22
    See application file for complete search history.

(56) References Cited

U.S. PATENT DOCUMENTS

| | | | |
|---|---|---|---|
| 9,732,049 | B2 | 8/2017 | Racine |
| 2017/0057936 | A1 | 3/2017 | Nosopharm |
| 2019/0309013 | A1 | 10/2019 | Zitterbart et al. |

FOREIGN PATENT DOCUMENTS

| | | | | |
|---|---|---|---|---|
| CN | 105601718 | A | 5/2016 | |
| EP | 3299085 | A1 * | 3/2018 | ................ A61P 1/00 |
| EP | 3299085 | A1 | 3/2018 | |
| JP | H11505208 | A | 5/1999 | |
| JP | 2002525263 | A | 8/2002 | |
| JP | 2015508666 | A | 3/2015 | |
| JP | 2016532705 | A | 10/2016 | |
| WO | 1996030399 | A1 | 10/1996 | |
| WO | 2000005251 | A1 | 2/2000 | |
| WO | 2013129926 | A1 | 9/2013 | |
| WO | 2015028966 | A2 | 3/2015 | |
| WO | 2015128504 | A1 | 9/2015 | |
| WO | 2017129818 | A1 | 8/2017 | |

OTHER PUBLICATIONS

Paradis-Bas et al (Chem.Soc.Rev., 2016, 45, 631-654) (Year: 2016).*
Hossain et al (Bioconjugate Chem 2009, 20, 1390-1396) (Year: 2009).*
Lu et al (Bioconjugate Chem 2010, 21, 187-202) (Year: 2010).*
International Search Report and Written Opinion, dated Feb. 13, 2020.
Alessia Amore et al, "Development of a Hypersensitive Periodate-Cleavable Amino Acid that is Methionine- and Disulfide-Compatible and its Application in MHC Exchange Reagents for T Cell Characterisation", CHEMBIOCHEM, vol. 14, No. 1, Jan. 2, 2013 (Jan. 2, 2013), p. 123-131.
Geoffray Leriche et al, "Cleavable linkers in chemical biology", Bioorganic & Medicinal Chemistry vol. 20, Issue 2, Jan. 15, 2012, pp. 571-582. https://doi.org/10.1016/j.bmc.2011.07.0484.
Vadim S. Korotkov et al., "Synthesis and biological activity of optimized belactosin C congeners", Organic & Biomolecular Chemistry,vol. 9, No. 22, Jan. 1, 2011 (Jan. 1, 2011), p. 7791.
Xiao-Yi Xiao, et al., A Cyclitively Cleavable Linker for Alcohols: Linker Preparation and Cleavage Conditions, J. Comb. Chem. 1999,1, 379-382.
Alessia Amore, et al., Development of a Hypersensitive Periodate-Cleavable Amino Acid that is Methionine- and Disulfide-Compatible and its Application in MHC Exchange Reagents for T Cell Characterisation, ChemBioChem 2013, 14, 123-131.
Vincent Aucagne, et al., Towards the Simplification of Protein Synthesis: Iterative Solid-Supported Ligations with Concomitant Purifications, Angew. Chem. Int. Ed. 2012, 51, 11320 -11324.
Canne, et al., Synthesis of a Versatile Purification Handle for Use with Boc Chemistry Solid Phase Peptide Synthesis, Tetrahedron Letters, vol. 38, No. 19, pp. 3361-3364,1997.
Funakoshi, et al., Affinity purification method using a reversible biotinylating reagent for peptides synthesized by the solid-phase technique, Journal of Chromatography, 638 (1993) 21-27.
Funakoshi, et al., Chemoselective one-step purification method for peptides synthesized by the solid-phase technique, Proc Natl Acad Sci. USA vol. 88, pp. 6981-6985, Aug. 1991, Biochemistry.
Hara, et al., Peptide purification by affinity chromatography based on alpha-ketoacyl group chemistry, J. Pept. Sci. 2009; 15: 369-376.
Hara, et al., Peptide purification using the chemoselective reaction between N-(methoxy)glycine and sothiocyanatofunctionalized resin, J. Pept. Sci 2016; 22: 379-382.
Jacobsen, et al., A Helping Hand to Overcome Solubility Challenges in Chemical Protein Synthesis, J. Am. Chem. Soc 2016, 138, 11775-11782.
Kim et al., IFettaercile Synthesis of N-(9-Fluorenylmethyloxycarbonyl)-3-amino-3-(4,5-dimethoxy-2-nitrophenyl) propionic Acid as a Photocleavable Linker for Solid-Phase Peptide Synthesis, Synle I I 2013, 24, 0733-0736.

(Continued)

*Primary Examiner* — Sudhakar Katakam
(74) *Attorney, Agent, or Firm* — Charney IP Law LLC; Thomas M. Finetti

(57) ABSTRACT

The present invention provides a new building block for peptide synthesis, which introduces a cleavage site that can be used to generate cleavable fragments subsequent to a peptide sequence.

10 Claims, 10 Drawing Sheets

Specification includes a Sequence Listing.

(56) References Cited

OTHER PUBLICATIONS

Korotkov, et al., Synthesis and biological activity of optimized belactosin C congeners, Org. Biomol. Chem., 2011, 9, 7791-7798.
Korotkov, et al., Synthesis and biological activity of optimized belactosin C congeners, Org. Biomol. Chern., 2011, 9, 7791-7798.
Leriche, et al., Cleavable linkers in chemical biology, Bioorganic & Medicinal Chemistry 20 (2012) 571-582.
Lu, et al., Chemical Strategies for the Synthesis of Peptide-Oligonucleotide Conjugates, Bioconjugate Chern. 2010, 21, 187-202.
Reiman, et al., Traceless Purification and Desulfurization of Tau Protein Ligation Products, Angew. Chern. Int. Ed. 2015, 54,306-310.
Scott, et al., Diversity Linker Units for Solid-Phase Organic Synthesis, Eur. J. Org. Chern. 2006,2251-2268.
Venkatesan, et al., Peptide Conjugates of Oligonucleotides: Synthesis and Applications, Chern. Rev. 2006, 106, 3712-3761.
Vizzavona, et al., Covalent capture purification of polypeptides after SPPS via a linker removable under very mild conditions. Tetrahedron Letters 43 (2002) 8693-8696.

\* cited by examiner

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: peptide sequence

<400> SEQUENCE: 1

Lys Ala Thr Ser Gly Gly Leu Phe
1               5

<210> SEQ ID NO 2
<211> LENGTH: 15
<212> TYPE: PRT
<213> ORGANISM: Artificial Sequence
<220> FEATURE:
<223> OTHER INFORMATION: peptide protein

<400> SEQUENCE: 2

Gly Ile Ser Phe Ser Ile Arg Phe Ala Ile Trp Ile Arg Phe Gly
1               5                   10                  15
```

```
<210> SEQ ID NO 3
<211> LENGTH: 20
<212> TYPE: PRT
<213> ORGANISM: Artificial Sequence
<220> FEATURE:
<223> OTHER INFORMATION: peptide protein

<400> SEQUENCE: 3

Lys Lys Lys Lys Lys Gly Ile Ser Phe Ser Ile Arg Phe Ala Ile Trp
1               5                   10                  15

Ile Arg Phe Gly
            20

<210> SEQ ID NO 4
<211> LENGTH: 9
<212> TYPE: PRT
<213> ORGANISM: Artificial Sequence
<220> FEATURE:
<223> OTHER INFORMATION: peptide protein

<400> SEQUENCE: 4

Ile Ile Lys Lys Ser Thr Ala Leu Leu
1               5

<210> SEQ ID NO 5
<211> LENGTH: 11
<212> TYPE: PRT
<213> ORGANISM: Artificial Sequence
<220> FEATURE:
<223> OTHER INFORMATION: peptide protein

<400> SEQUENCE: 5

Ala Phe Asp Tyr Leu Ala Gln Tyr His Gly Gly
1               5                   10

<210> SEQ ID NO 6
<211> LENGTH: 57
<212> TYPE: PRT
<213> ORGANISM: Artificial Sequence
<220> FEATURE:
<223> OTHER INFORMATION: peptide protein

<400> SEQUENCE: 6

Trp Trp Trp Trp Glu Ala Ala Glu Ala Ala Glu Ala Ala
1               5                   10                  15

Glu Ala Ala Glu Ala Ala Glu Ala Ala Glu Ala Ala
            20                  25                  30

Glu Ala Ala Glu Ala Ala Glu Ala Ala Glu Ala Ala
                35                  40                  45

Glu Ala Ala Glu Glu Glu Glu Glu
        50                  55
```

CLEAVABLE LINKER FOR PEPTIDE SYNTHESIS

The present invention relates to the technical field of peptide synthesis. More precisely, the present invention provides a new possibility to introduce cleavable linkers into chemically synthesized peptides, thereby creating new peptide conjugates.

PRIOR ART

Cleavable linkers, defined as chemical moieties which connect two functionalities through a cleavable bond, are important tools in solid phase synthesis (SPS) and chemical biology. Especially in solid phase peptide synthesis (SPPS) these linkers can help solving issues regarding the physicochemical properties, handling and purification of peptides: Through a cleavable linker peptides can be modified with functional tags (for example solubility enhancing moieties) and after the cleavage of the linker the desired peptide is released, with or without a residue of the linker. Cleavable linkers are widely used in organic synthesis and solid phase synthesis (see for example Leriche et al., Bioorg. Med. Chem. 2012, 20, 571-582; Scott et al., Eur. J. Org. Chem. 2006, 2251-2268). Cleavage may be performed by chemical (nucleophiles, basic reagents, electrophiles, acidic reagents, reducing reagents, oxidizing reagents, organometallic and metal catalysts), by photochemical or enzymatic means. In peptide synthesis cleavable linkers are mainly used to link the nascent peptide to a resin which can be cleaved off after completion of solid phase peptide synthesis (see for example Novabiochem Peptide Synthesis Catalogue, Merck; Jensen et al. (Ed.), Peptide Synthesis and Application, Methods in Molecular Biology, Vol. 1047, Springer Protocols, Humana Press, Springer, New York, 2013).

For internal incorporation into a peptide sequence cleavable linker building blocks have also been described. α,γ-Diamino-β-hydroxybutanoic acid and γ-amino-α,β-dihydroxybutanoic acid based linker building blocks for peptide synthesis have been described by Amore et al., Chem Bio Chem 2013, 14, 123-131. These linkers can be cleaved by oxidative means, i.e. using sodium periodate. Disadvantageous may be oxidation of oxidation sensitive components within the peptide like cysteine or methionine residues.

Photocleavable linker building blocks for peptide synthesis which have been described by Kim et al., Synlett 2013, 24, 733-736 are another example. Disadvantages of photoirradiation may be incomplete linker cleavage and side reactions arising from radical reactions. A cyclitively cleavable linker for alcohols based on [2-(aminomethyl)phenyl]acetic acid has been described by Xiao et al., J. Comb. Chem. 1999, 1, 379-382. This linker has only been applied for the synthesis and release of alcohols by using a solid support. A derivative which can be used for internal incorporation in peptide synthesis has not been described. Peptide synthesis applying cleavable solubilizing tags has been described using different chemistries and cleavage conditions (see for example: Jacobsen et al., JACS 2016, 138, 11777-11782; WO 2016047794).

Peptide synthesis applying cleavable purification tags has been described using different chemistries and cleavage conditions (see for example: Funakoshi et al., Proceedings of the National Academy of Sciences 1991, 88, 6981-6985; Funakoshi et al., J. Chromatogr. 1993, 638, 21-27; Canne, et al. Tetrahedron Letters 1997, 38, 3361-3364; Vizzavona et al., Tetrahedron Letters 2002, 43, 8693-8696; Hara et al., Journal of Peptide Science, 2009, 15, 369-376; Aucagne et al., Angewandte Chemie International Edition 2012, 51, 11320-11324; Reimann et al., Angewandte Chemie International Edition 2015, 54, 306-310; Hara et al., Journal of Peptide Science, 2016, 15, 379-382; Patents: Aucagne et al. WO 2011058188, Zitterbart et al. WO 2017129818 A1). In this approach, the linkers are usually attached in the last cycle of SPPS to the N-terminus of the growing peptide chain to enable selective immobilization of the desired full-length peptide onto a solid support. Side products are removed by washing the solid support and eventually the target peptide is released by cleavage of the linker. The cleavable linkers used for non-chromatographic purification of peptides usually require strong basic conditions. Under these conditions undesired side-reactions might occur e.g. racemization. A major problem of the frequently used sulfonate-elimination linkers are the highly reactive electrophiles, which are generated during the cleavage reaction. These intermediates react rapidly with the nucleophilic side-chain groups (e.g. arginine, cysteine) and consequently limit the application of the sulfonate based cleavable linkers. The rather rare example of an oxidatively cleavable purification linker from Vizzavona et al. (Tetrahedron Letters 2002, 43, 8693-8696) circumvent the aforementioned problems, but is most likely not compatible with methionine or cysteine containing peptides.

Isoacyl dipeptides are tools for enhancing synthetic efficiency in Fmoc SPPS (Y. Sohma et al., Chem. Commun. 2004, 124-125). Isoacyl dipeptides consist of a Boc-protected serine or threonine derivative in which the β-hydroxyl group is acylated by a Fmoc-protected amino acid. After incorporation of an isoacyl dipeptide building block within the sequence of a peptide, the secondary structure of the peptide is changed enabling more efficient synthesis. Furthermore, after cleavage and deprotection the isoacyl form of the peptide can be purified by HPLC. At pH 7.4 O→N intramolecular acyl migration takes place to generate the regularly amide linked peptide. Applying these isoacyl dipeptide building blocks no cleavage reaction can be performed.

Peptide-oligonucleotide conjugates are an emerging class for therapeutic and diagnostic applications. However, the synthesis of these conjugates remains a major challenge (see reviews of N. Venkatesan et al., Chemical Reviews 2006, 106, 3712-3761 and K. Lu et al., Bioconjugate Chemistry 2010, 21, 187-202). A straight forward approach would be to assemble the desired peptide-oligonucleotide conjugates on a polymeric support by means of solid-phase based synthesis. Unfortunately, established methods of solid-phase oligonucleotide and peptide synthesis are not fully compatible. The solid-phase synthesis of peptides requires the use of strong acids and thereby prevents the synthesis of peptide-oligonucleotide conjugates due to instability of oligonucleotides under acidic conditions. This is why the stepwise synthesis of peptide-oligonucleotide conjugates usually proceeds by first assembling the peptide, followed by oligonucleotide synthesis on the same solid support. Albeit this strategy has been successfully applied for the synthesis of rather simple peptide-oligonucleotide conjugates, the method is still lacking the full spectrum of compatible protecting groups to address the challenging chemistry of the amino acids side chains. Conclusively, a reliable and general applicable method for the stepwise solid-phase based synthesis of peptide-oligonucleotide conjugates is not available. Therefore, the synthesis of peptide-oligonucleotide conjugates usually proceeds by employing a convergent strategy. Here the peptide and the oligonucleotide fragments are synthesized separately by using routine building blocks and protocols of solid-phase synthesis. After purification the two fragments are conjugated and the desired peptide-oligonucleotide conjugate is isolated after an additional purification step. Low overall yields, increased expenditure of time and high costs are the major disadvantages of this strategy, which result from the aforementioned numerous purification steps and intermediate lyophilization procedures. Moreover, HPLC-based purification steps and intermediate lyophilization imped the possibility of achieving a high-throughput synthesis of peptide-oligonucleotide conjugates by means of automation. These drawbacks become particularly troublesome, if a large number of peptide-oligonucleotide conjugates needs to be synthesized, which is required e.g. for screening a suitable transfection peptide on a known antisense oligonucleotide. A perfect method would combine the ease of established solid-phase synthesis and post-synthetic conjugation while bypassing the need of any HPLC-based purification.

However, all the above disclosed methods for applying cleavable linkers for peptide synthesis have several disadvantages like inefficient incorporation or cleavage, harsh, damaging cleavage conditions, complex reagent synthesis or restricted use.

BRIEF DESCRIPTION OF THE INVENTION

The present invention therefore provides a building block comprising the structure

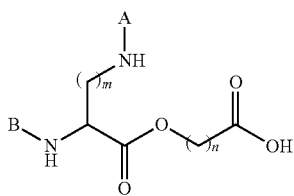

wherein 2≤n≤24, m=2 or 3, and A and B are protective groups. Usually, A and B are orthogonal protective groups which are cleaved under different conditions. In one embodiment, A is an acid labile protective group and B is a tag or base labile protective group. In one particular embodiment, A is Boc and/or B is Fmoc.

In a second aspect, the present invention provides a compound comprising the structure

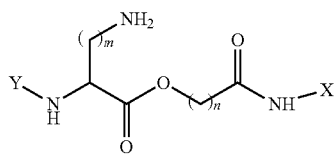

wherein 2≤n≤24, m=2 or 3, X is a peptide, or a solid support and Y is selected from a group consisting of a peptide, a functional group, a tag, and a peptide containing a functional group or a tag.

In one embodiment, Y is either a solubility enhancing tag, an immobilization tag or a solid phase. For example, Y may be selected from a group consisting of PEG, poly-lysine, poly-arginine, poly-glutamic acid, and poly-aspartic acid. Y may also be selected from a group consisting of biotin, hydrazine, aminooxy, azide, alkynyl, alkenyl, aldehyde, ketone, pyrroloalanine, carboxy and thiol.

In a third aspect, the present invention provides a method comprising the steps of synthesizing a peptide on a solid support, said peptide comprising a terminal amino group,
providing a building block as disclosed above, and
coupling said building block to said peptide.
Said method may further comprise the steps
removing protective group B, and
coupling at least one amino acid building block to the terminal amino group.
Alternatively, said method may further comprise steps
removing protective group B,
optionally coupling at least one amino acid building block to the terminal amino group, and
coupling a tag or a functional group to the terminal amino group.
Said functional group or tag may be selected from a group consisting of PEG, poly-lysine, poly-arginine, poly-glutamic acid, poly-aspartic acid, biotin, hydrazine, aminooxy, azide, alkynyl, alkenyl, aldehyde, pyrroloalanine, carboxy, and thiol.

In addition, the methods disclosed above may further comprise the step of
removing protective group A at a pH≤6, thereby also removing other protective groups present on said peptide and cleaving said peptide from the solid support, which may occur at a pH≥8.

In one embodiment, the present invention provides a method comprising the steps of
a) synthesizing a peptide on a solid support, said peptide comprising a terminal amino group,
b) providing a building block as disclosed above, and
c) coupling said building block to said peptide
d) removing protective group B,
e) optionally coupling at least one amino acid building block to the terminal amino group, and
f) coupling a solubilizing or immobilizing tag to the terminal amino group,
and further comprising the steps
g) removing protective group A at a pH≤6, thereby also removing other protective groups present on said peptide and cleaving said peptide from the solid support
h) purifying said peptide, and
i) cleaving off said solubilizing tag at a pH≥8, or
g) removing protective group A at a pH≤6, thereby also removing other protective groups present on said peptide and cleaving said peptide from the solid support
h) immobilizing said peptide via said immobilizing tag on a solid support
i) optionally conjugating said peptide to an additional chemical entity, and
j) cleaving off said immobilizing tag at a pH≥8.
Said chemical entity may be a carbohydrate, a protein, a peptide, a dye, a hapten, or the like. In particular, said chemical entity may be a nucleic acid, oligonucleotide or nucleotide containing compound, preferably a nucleoside-hexaphosphate.

BRIEF DESCRIPTION OF FIGURES

FIG. 1A illustrates peptide synthesis.
FIG. 1B illustrates solvation in 0.05 M NaHCO₃ solution (pH=8.2), triggering cyclization.
FIG. 1C depicts a series of LC-MS chromatograms showing cleavage of peptide AB into A and B over time.

FIG. 2A depicts the cleavage of poly-lysine tag from insoluble peptide.

FIG. 2B provides a LC-MS chromatogram of H-KKKKK1AhaGISFSIRFAIWIRFG-NH2 (10) (SEQ ID NO: 3).

FIG. 2C provides a MS (ESI) of insoluble peptide 12.

FIG. 3A depicts a crude peptide mixture after SPPS and cleavage from resin.

FIG. 3B illustrates supernatant after 30 min.

FIG. 3C depicts supernatant after incubation with 0.02 M $NH_4HCO_3$ (pH=8.8) for 30 min.

FIG. 5A depicts a chromatogram of the crude material after SPPS.

FIG. 5B depicts a chromatogram after washing the supernatant containing deletions.

FIG. 5C depicts a chromatogram of the pure peptide.

FIG. 5D depicts a chromatogram of the pure peptide nucleotide conjugate.

SEQUENCE LISTING

Figure 1A:
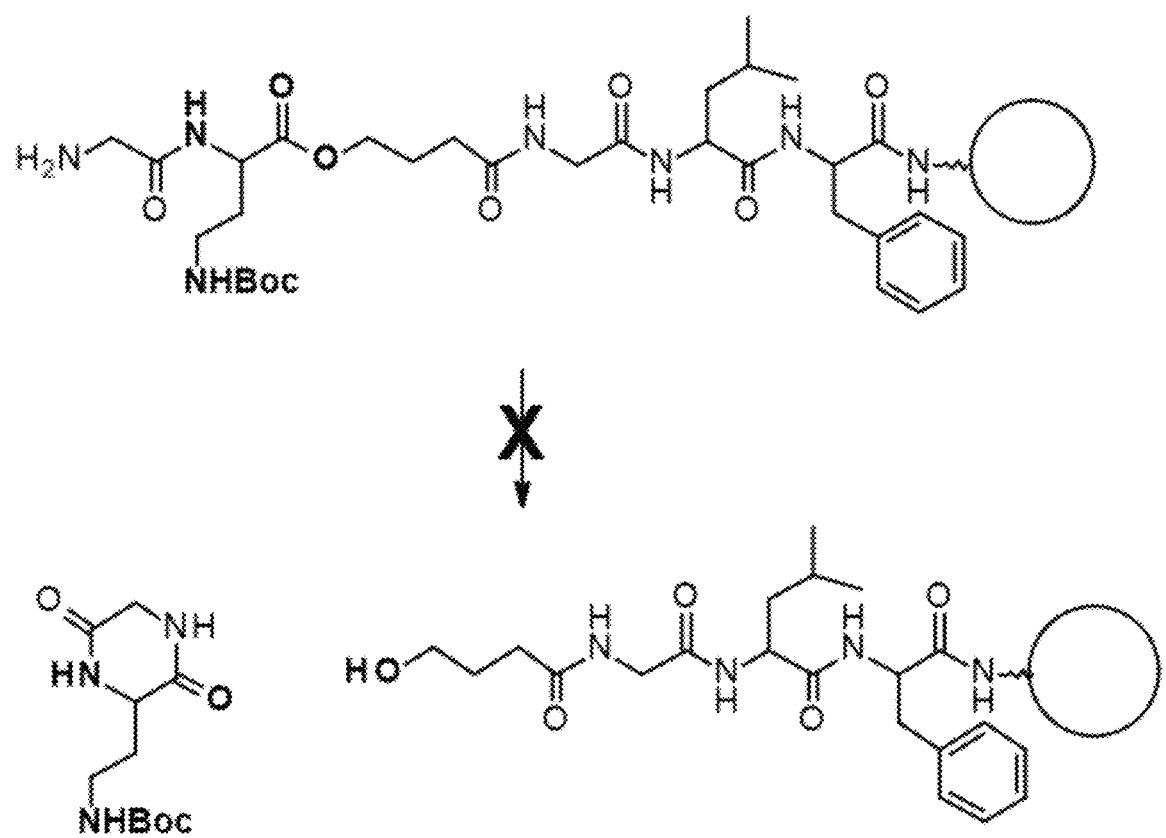
FIGS. 1A-1C illustrate peptide synthesis according to example 3, where the method comprises introduction of a linker.

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "P34958-WO_ST25.txt" created on Jan. 12, 2021, 2 KB, which is incorporated by reference herein.

DETAILED DESCRIPTION OF THE INVENTION

List of definitions and abbreviations:
Fmoc: Fluorenylmethyloxycarbonyl
Boc: tert-Butyloxycarbonyl
SPPS: Solid Phase Peptide Synthesis
SPS: Solid Phase Synthesis
TFA: Trifluoroacetic acid
DBU: 1,8-Diazabicyclo[5.4.0]undec-7-ene
DMF: N,N-Dimethylformamide
DAB: Diamino butyric acid
EDC: N-(3-Dimethylaminopropyl)-N'-ethylcarbodiimide
DMAP: N,N-Dimethylpyridin-4-amine
HATU: 1-[Bis(dimethylamino)methylene]-1H-1,2,3-triazolo[4,5-b]pyridinium 3-oxide hexafluorophosphate
DIPEA: N,N-Diisopropylethyl amine
THPTA: Tris(3-hydroxypropyltriazolylmethyl)amine
Pra: Propargylglycine
Aha: Azidohomoalanine
TIS: Triisopropyl silane Definitions Tag: In the context of the present invention, a tag is a chemical moiety which alters the chemical or physical properties of a molecule and/or renders the molecule recognizable. For example, a purification tag may facilitate purification of a molecule. A tag may be an immobilization tag, i.e. a chemical moiety that can be attached to a solid support. A tag may also be a solubility enhancing tag, that means a chemical group which if present increases the solubility of a certain molecule.

Functional Group: Functional groups are specific chemical groups (moieties) of atoms or bonds within molecules that are responsible for the characteristic chemical reactions of those molecules. Functional groups are specific substituents or moieties within molecules that are responsible for the characteristic chemical reactions of those molecules. The same functional group will undergo the same or similar chemical reaction(s) regardless of the size of the molecule it is a part of. This allows for systematic prediction of chemical reactions and behavior of chemical compounds and design of chemical syntheses. Furthermore, the reactivity of a functional group can be modified by other functional groups nearby. In organic synthesis, functional group interconversion is one of the basic types of transformations. Functional groups are groups of one or more atoms of distinctive chemical properties no matter what they are attached to. The atoms of functional groups are linked to each other and to the rest of the molecule by covalent bonds. For repeating units of polymers, functional groups attach to their nonpolar core of carbon atoms and thus add chemical character to carbon chains. Functional groups can also be charged.

Protecting group: The term "protective group" or its synonym "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Protecting groups are amino-protecting groups, carboxy-protecting groups or hydroxy-protecting groups. A protecting group or protective group or blocking group is introduced into a molecule by chemical modification of a functional group to obtain chemoselectivity in a subsequent chemical reaction. A protecting group is introduced to block or at least reduce the reactivity of functional groups. A deprotection is a chemical step of removal of a protecting group. Relevant protective groups in the field of peptide synthesis are base labile protecting groups and acid labile protecting groups. Base labile protecting groups are cleaved off at a pH between 7.5 and 12, but preferably at a pH between 8.0 and 10. Acid labile protective groups are cleaved off at a pH between 6.5 and 3, but preferably at a pH between 6.0 and 5. For the present invention, amino protecting groups are of particular importance. Amino-protecting groups are groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Examples of these groups are found in T. W. Greene and P. G. M. Wuts, "Protective Groups in Organic Synthesis," 2nd ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

Peptide: A peptide is a chain of amino acid building blocks linked through amide bonds with a length of 2 to 120 residues.

Novel cleavable linkers for peptide synthesis have been developed. Cleavage occurs under mild basic conditions. The linkers are based on a 4-aminobutanoate core which undergoes intramolecular lactamization at pH>8 cleaving the ester bond by releasing two fragments, the N-terminal alcohol and the C-terminal lactam (Scheme 1A). As Nα-Fmoc-Nγ-Boc-protected building block (Scheme 1B) this aminobutanoate cleavable linker can be employed in solid phase peptide synthesis. Aminobutanoate linker 1 turned out to be stable during conventional peptide synthesis and surprisingly during an Fmoc deprotection of the successive amino acid no cyclization to a 6 membered diketopiperazine and the corresponding breakup peptide was observed.

Schemes 1A and 1B

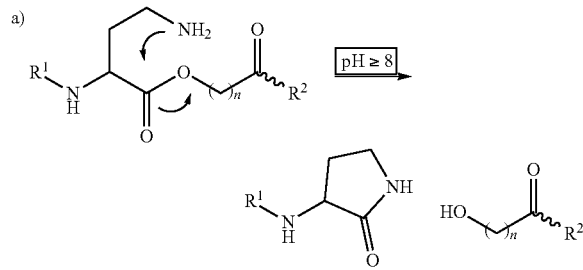

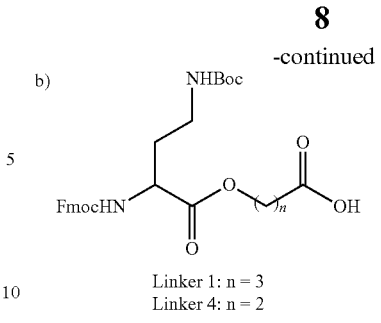

Linker 1: n = 3
Linker 4: n = 2 a) Cyclitively cleavage of the linker (n > 1).
b) General formula of protected cleavable linker (n > 1).

During solid phase peptide synthesis the Nγ-Boc protected amino group is unreactive and aminobutanoate linker remains intact. Cleavage of the peptide from the solid support and deprotection of protecting groups under acidic conditions leads to removal of the Nγ-Boc protecting group of the aminobutanoate linker. Since the amino group is protonated under the acidic cleavage and deprotection conditions the lactamization reaction is fully suppressed and the aminobutanoate linker remains intact. The peptide containing the intact aminobutanoate linker can therefore also be purified under acidic conditions (i.e. water/acetonitrile/trifluoroacetic acid eluent). Under mild basic conditions the cleavage of the aminobutanoate linker proceeds by means of an intramolecular cyclization reaction, releasing two peptides, one as a N-alcohol and the other as a C-terminal lactam. The general concept is shown in Scheme 2 which shows solid phase peptide synthesis with an aminobutanoate linker (n>1) and final cleavage with release of two peptide fragments.

Scheme 2

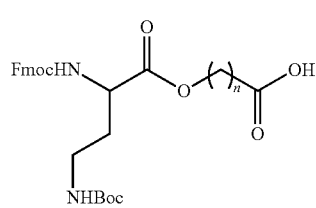 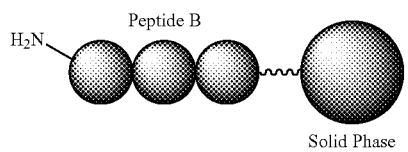

↓ SPS

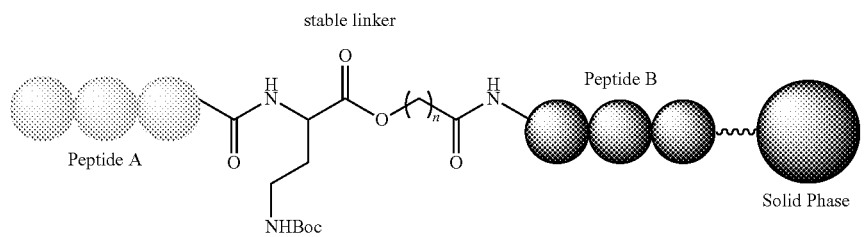

↓ TFA

-continued stable linker

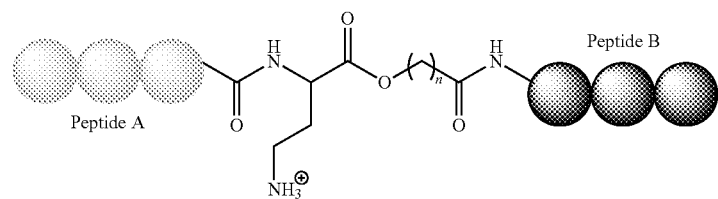

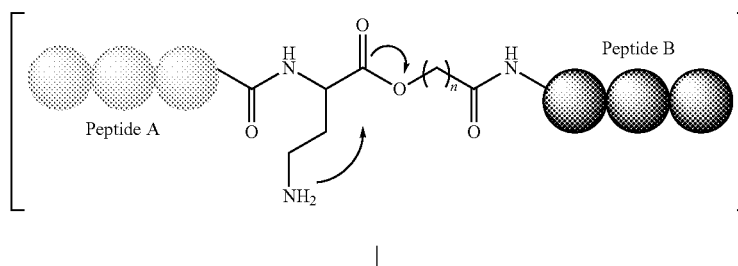

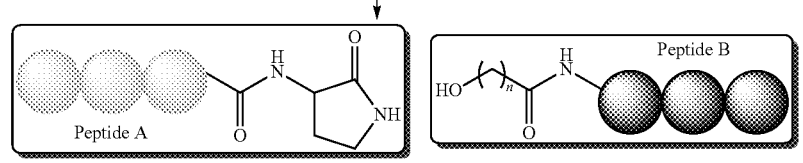

It has been found that a cleavable linker with n=1 is not suited since side reactions occurred during solid phase peptide synthesis (i.e. ester cleavage). However, cleavable linkers with n=2 and n=3 were compatible with solid phase peptide synthesis and yielded the desired linker-containing peptides, which could be cleaved under mild alkaline conditions. Therefore the above mentioned building blocks can be used to add a variety of functional groups to the N-terminus of a peptide which can be removed at a later process step.

One application of adding a cleavable functional group is to introduce a hydrophilic tag onto the N-terminus of a hydrophobic peptide in order to enable the purification (i.e. by HPLC) of such a hydrophobic peptide. After purification, the solubilizing tag can be cleaved off under mild basic conditions in order to release the purified hydrophobic target peptide.

The method can also be applied for an improved synthesis of oligonucleotide-peptide conjugates. This is of particular interest if the peptide contains many hydrophobic residues. For instance, the hydrophobic peptide can be synthesized first, containing a conjugation site for the attachment of the oligonucleotide, such as azidohomoalanine. Then the cleavable aminobutanoate linker is coupled, followed by introduction of a solubilizing tag sequence. After cleavage and deprotection the peptide can be purified by HPLC and finally be conjugated to an oligonucleotide functionalized with a conjugation site. Said conjugation site, for example, may be an alkyne group. Thereafter the conjugate can be purified and the solubilizing tag can be cleaved off under mild alkaline conditions.

Another application is the introduction of a purification tag which may be introduced at the N-terminus of a peptide. Biotin is a prominent example for such a purification tag. First, peptide is synthesized via SPPS including a capping step after each coupling. Thereafter the cleavable linker is coupled to the N-terminus of the peptide and finally biotin is coupled onto the cleavable linker. After cleavage and deprotection under acidic conditions, the biotin labeled peptide can be bound to streptavidin coated beads, which are preferably magnetic beads. Non-biotinylated by-products of SPPS (i.e. failure sequences, deletions) can be removed by washing. Thereafter, the purified peptide can be released from the streptavidin beads by cleaving the linker under mild alkaline treatment.

Contemporary methods for the convergent synthesis of peptide-oligonucleotide conjugates require multiple purification steps. Therefore, the screening of numerous peptide-oligonucleotide conjugates is a time-and cost-consuming endeavor. The method of the invention enables the rapid synthesis of peptide-(oligo)nucleotide conjugates. The method of the invention using the cleavable linker building block of the invention circumvents the need of tedious HPLC-purification steps by the combination of chemoselective reactivity units and cleavable purification tags and allowing for mild cleavage of the molecule of interest. This non-chromatographic purification approach enables the parallel synthesis of numerous conjugates in good yield and purity.

As will be shown within the examples, the cleavable linker of the invention is easy to synthesize, allows efficient incorporation into peptides and mild cleavage under slightly alkaline, non-destructing conditions.

EXAMPLES

Example 1: Synthesis of Linker 1 (m=2; n=3)

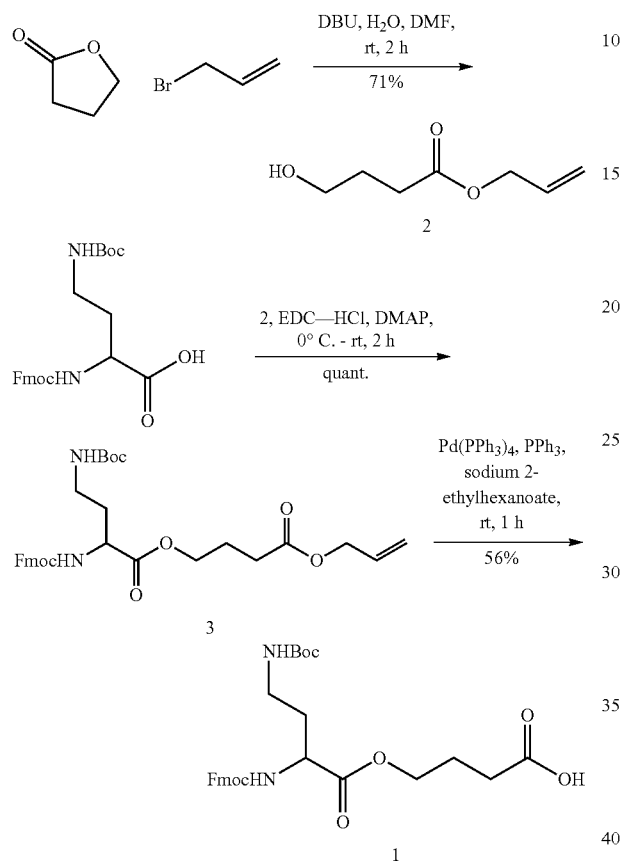

Synthesis of Compound 2

Allyl 4-Hydroxybutanoate

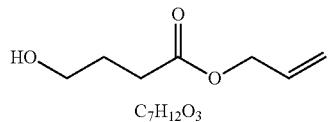

To a solution of γ-butyrolactone (5.00 g, 58.1 mmol) in DMF (17 ml) were added H$_2$O (13.6 g, 13.6 ml, 755 mmol) and DBU (8.85 g, 8.67 ml, 58.1 mmol). After 1 h stirring at r.t. allyl bromide (10.5 g, 7.53 ml, 87.2 mmol) was added to the solution. The reaction was quenched after 1 h by addition of sat. aq. NH$_4$Cl solution (30 ml) and the aqueous phase was extracted with ethyl acetate (3×100 ml). The combined organic layers were dried over Na$_2$SO$_4$ and the solvent was removed under reduced pressure. Column chromatography over SiO$_2$ (n-hexane/ethyl acetate=1:1) afforded the desired product (5.90 g, 40.9 mmol, 71%) as a colorless oil.

R$_f$ (n-hexane/ethyl acetate=1:1)=0.33 (KMnO$_4$)

$^1$H-NMR (400 MHz, CDCl$_3$): δ=6.06-5.86 (m, 1H), 5.42-5.04 (m, 2H), 4.59 (td, J=1.4, 5.7 Hz, 1H), 4.35 (t, J=7.0 Hz, 1H), 4.25-4.06 (m, 1H), 3.73-3.67 (m, 1H), 2.55-2.41 (m, 2H), 2.34-2.16 (m, 1H), 1.99-1.83 (m, 1H), 1.62 (s, 1H).

Synthesis of Compound 3

4-(Allyloxy)-4-oxobutyl 2-((((9H-fluoren-9-yl)methoxy)carbonyl)amino)-4-((tert-butoxycarbonyl)amino)butanoate

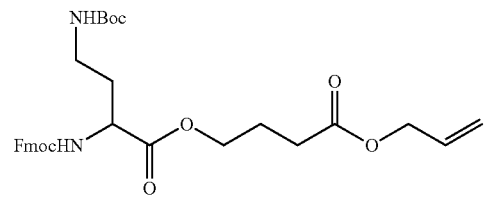

Commercially available Fmoc-Dab(Boc)-OH (1.00 g, 2.27 mmol) and compound 2 (360 mg, 2.50 mmol) were dissolved in CH$_2$Cl$_2$ (7.5 ml) and cooled to 0° C. EDC-HCl (479 mg, 2.50 mmol) and DMAP (28 mg, 0.227 mmol) were added to the solution. After 1 h stirring at r.t. sat. aq. NaCl solution (25 ml) was added to the reaction mixture which was then extracted with CH$_2$Cl$_2$ (3×50 ml). The combined organic layers were dried over Na$_2$SO$_4$ and the solvent was removed under reduced pressure affording the desired product (1.27 g, 2.24 mmol, 99%) as a colorless resin.

R$_f$ (n-hexane/ethyl acetate=1:1)=0.63

$^1$H-NMR (400 MHz, CDCl$_3$): δ=7.80-7.72 (m, 2H), 7.64-7.56 (m, 2H), 7.44-7.36 (m, 2H), 7.35-7.28 (m, 2H), 5.95-5.84 (m, 1H), 5.68-5.57 (m, 1H), 5.34-5.20 (m, 2H), 5.10-4.98 (m, 1H), 4.61-4.55 (m, 2H), 4.46-4.32 (m, 3H), 4.26-4.15 (m, 3H), 3.47-3.30 (m, 1H), 3.02-2.93 (m, J=5.3, 5.3, 8.3, 14.0 Hz, 1H), 2.46-2.37 (m, 2H), 2.12-1.94 (m, 3H), 1.82-1.72 (m, 1H), 1.51-1.35 (m, 9H).

MS (ESI): found 567.3 [M+H]$^+$, 467.3 [M+H−Boc]$^+$, calculated 567.3 [M+H]$^+$

Synthesis of Linker 1

4-((2-((((9H-fluoren-9-yl)methoxy)carbonyl)amino)-4-((tert-butoxycarbonyl)amino)butanoyl)oxy)butanoic acid

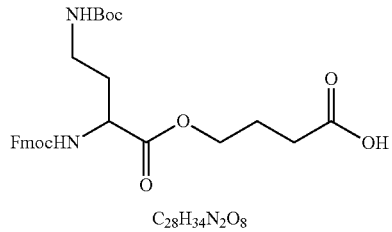

To a solution of 4-(allyloxy)-4-oxobutyl 2-((((9H-fluoren-9-yl)methoxy)carbonyl)amino)-4-((tert-butoxycarbonyl)amino)butanoate 3 (4.5 g, 7.94 mmol) in CH$_2$Cl$_2$/ethyl acetate 2:1 (75 ml) were added tetrakis(triphenylphosphine) palladium(0) (275 mg, 0.238 mmol), triphenylphosphine (104 mg, 0.395 mmol) and sodium 2-ethylhexanoate (1.97 g, 11.9 mmol). The reaction was stirred at r.t. for 3 hours. Then 1 M HCl (50 ml) was added. The reaction mixture was extracted with CH$_2$Cl$_2$ (3×150 ml). The combined organic layers were dried over Na$_2$SO$_4$ and the solvent was removed under reduced pressure. Column chromatography over SiO$_2$ (ethyl acetate+1% methanol) afforded the desired product 1 as a colorless solid.

R$_f$ (Ethyl Acetate)=0.38

$^1$H-NMR (400 MHz, CDCl$_3$): δ=7.79-7.73 (m, 2H), 7.64-7.55 (m, 2H), 7.44-7.37 (m, 2H), 7.35-7.28 (m, 2H), 5.70-5.54 (m, 1H), 5.18-5.02 (m, 1H), 4.47-4.33 (m, 3H), 4.28-4.16 (m, 3H), 3.43-3.32 (m, 1H), 3.04-2.94 (m, 1H), 2.55-2.25 (m, 3H), 2.15-1.98 (m, 3H), 1.48-1.38 (m, 9H).

MS (ESI): found 527.3 [M+H]$^+$, 427.2 [M+H−Boc]$^+$, calculated 527.2 [M+H]$^+$ Example 2: Synthesis of Linker 4 (m=2; n=2)

Scheme 4

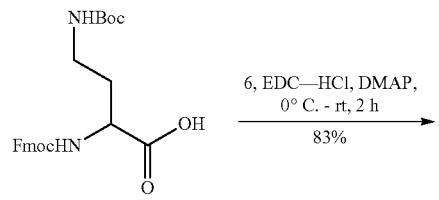

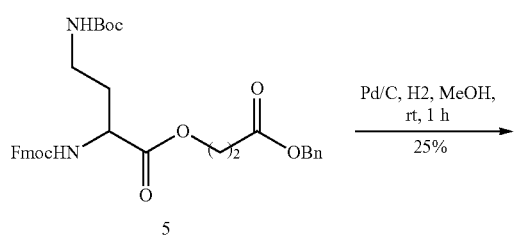

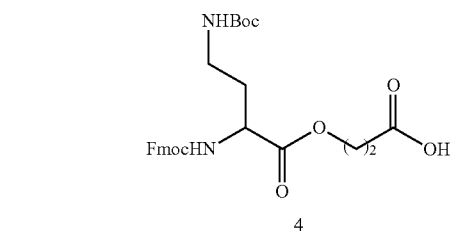

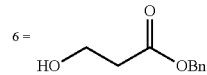

Synthesis of Compound 5

3-(benzyloxy)-3-oxopropyl 2-((((9H-fluoren-9-yl)methoxy)carbonyl)amino)-4-((tert-butoxycarbonyl)amino)butanoate

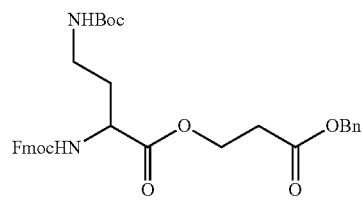

Commercially available Fmoc-Dab(Boc)-OH (2.5 g, 5.68 mmol) and benzyl 3-hydroxypropanoate (1.12 g, 6.25 mmol) were dissolved in CH$_2$Cl$_2$ (20 ml) and cooled to 0° C. To this solution EDC-HCl (1.20 g, 6.25 mmol) and DMAP (70.0 mg, 0.568 mmol) were added. After 1 h sat. aq. NaCl solution (25 ml) was added, the organic phase was separated and the aqueous phase was extracted with CH$_2$Cl$_2$ (3×50 ml). The combined organic layers were dried over Na$_2$SO$_4$ and the solvent was removed under reduced pressure. Column chromatography over SiO$_2$ (n-hexane/EtOAc 6:4) afforded the desired product (2.84 g, 4.71 mmol, 83%) as a colorless resin.

$^1$H-NMR (400 MHz, CDCl$_3$) δ=7.78-7.74 (m, 2H), 7.65-7.58 (m, 2H), 7.35 (s, 9H), 5.77-5.66 (m, 1H), 5.17-5.14 (m, 2H), 5.13-5.04 (m, 1H), 4.54-4.46 (m, 1H), 4.45-4.30 (m, 4H), 4.26-4.20 (m, 1H), 3.91-3.87 (m, 1H), 3.46-3.33 (m, 1H), 2.97-2.88 (m, 1H), 2.77-2.70 (m, 2H), 2.05-2.03 (m, 1H), 2.01-1.92 (m, 1H), 1.79-1.70 (m, 1H), 1.47-1.42 (m, 9H).

Synthesis of Compound 4

3-((2-((((9H-fluoren-9-yl)methoxy)carbonyl)amino)-4-((tert-butoxycarbonyl)amino)butanoyl)oxy)propanoic acid

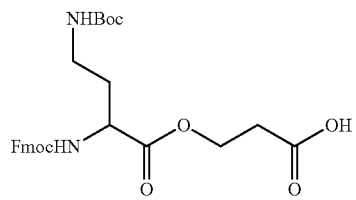

Compound 4 (2.8 g, 4.65 mmol) was dissolved in MeOH (50 ml). Palladium on carbon (Pd/C 10%, 742 mg, 0.69 mmol) was added to the solution and H$_2$ was bubbled into the reaction mixture. After 1 h the reaction was diluted with CH$_2$Cl$_2$ and filtered through a silica plug. Solvent was removed under reduced pressure affording the desired product (0.6 g, 1.17 mmol, 25%) as a colorless solid.

MS (ESI): 513.0 [M+H], calculated 513.2 [M+H]$^+$.

Example 3: Peptide Synthesis Applying Linker 1

Figure 1B:
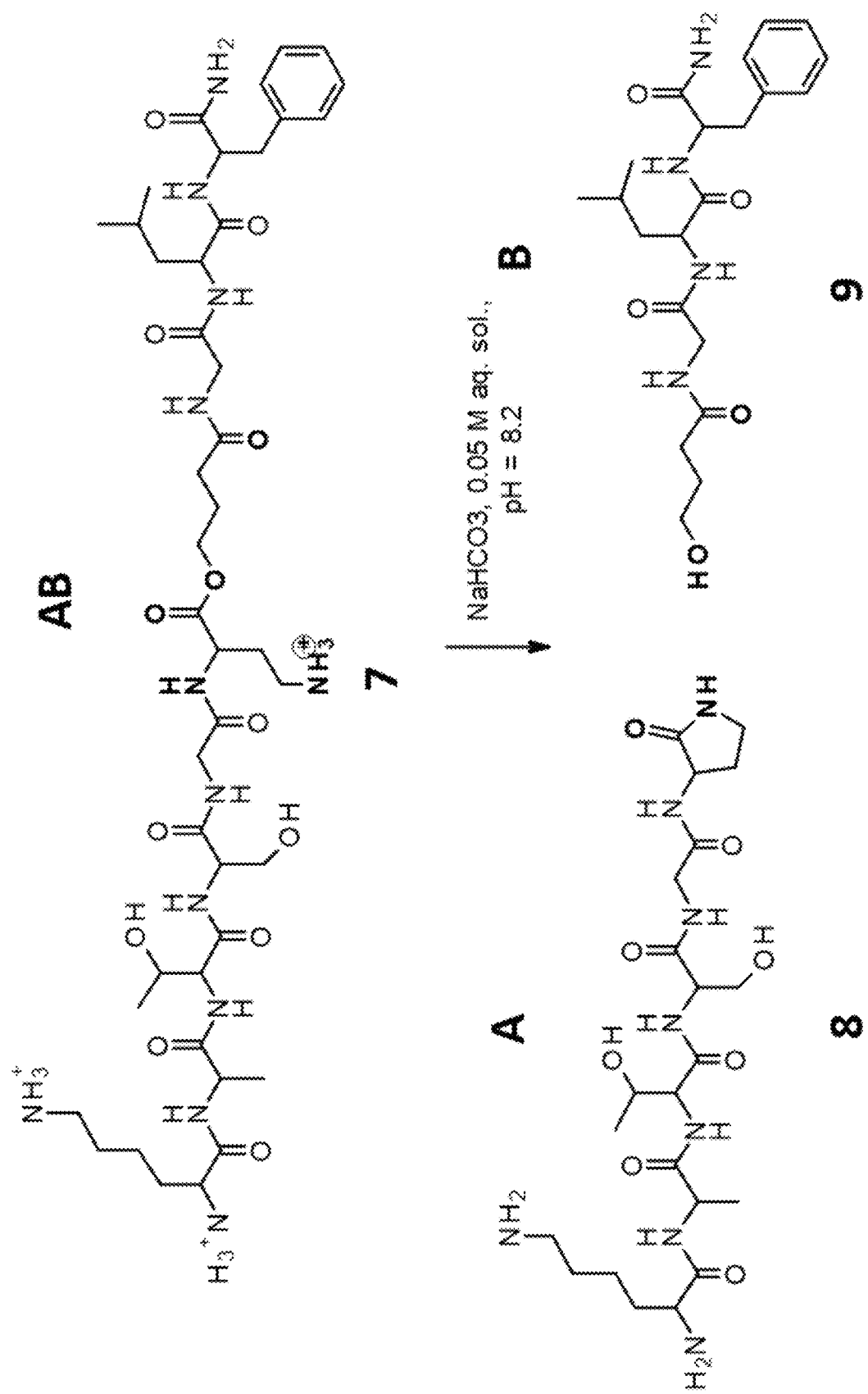
Figure 1C:
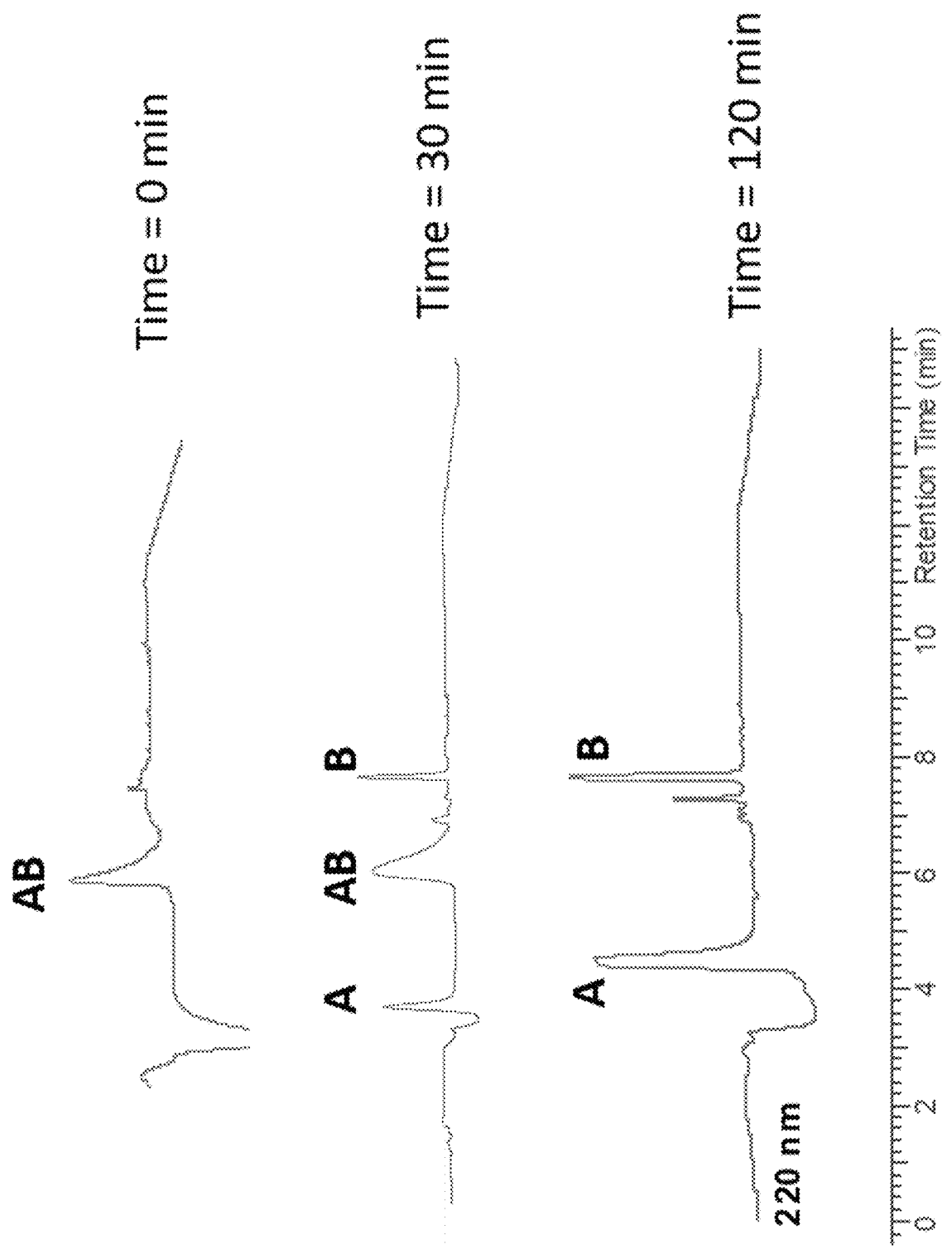

A peptide with the sequence H-KATSG—(linker 1)—GLF-NH$_2$ (7) (SEQ. ID. No: 1) was synthesized by solid phase peptide synthesis and purified by preparative HPLC. Linker 1 was stable during peptide synthesis, and surprisingly also during Fmoc deprotection with piperidine of the successive amino acid (Gly at position 5). No cyclization to a 6 membered diketopiperazine and the corresponding breakup peptide was observed (FIG. 1A). The purified peptide (AB in FIG. 1B) was then dissolved in 0.05 M NaHCO$_3$ solution (pH=8.2) which triggered the intramolecular cyclization reaction releasing the two fragments 8 and 9 (A and B, FIG. 1B), identified by LC-MS (FIG. 1C).

Example 4: Synthesis of Hydrophobic Peptide

Figure 2A:
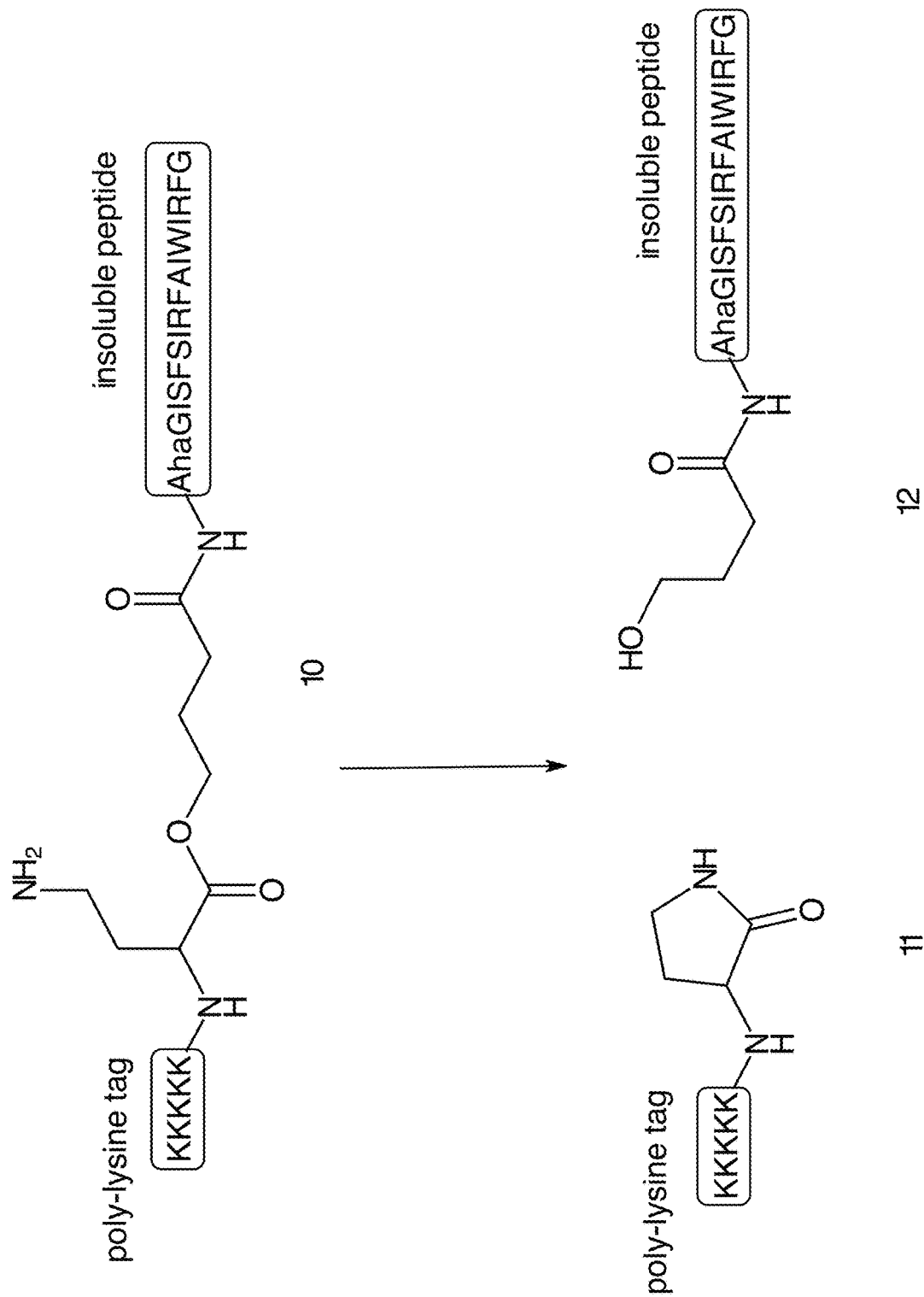
FIGS. 2A-2C illustrate the synthesis of a hydrophobic peptide according to example 4 (SEQ ID NO: 3).
Figure 2B:
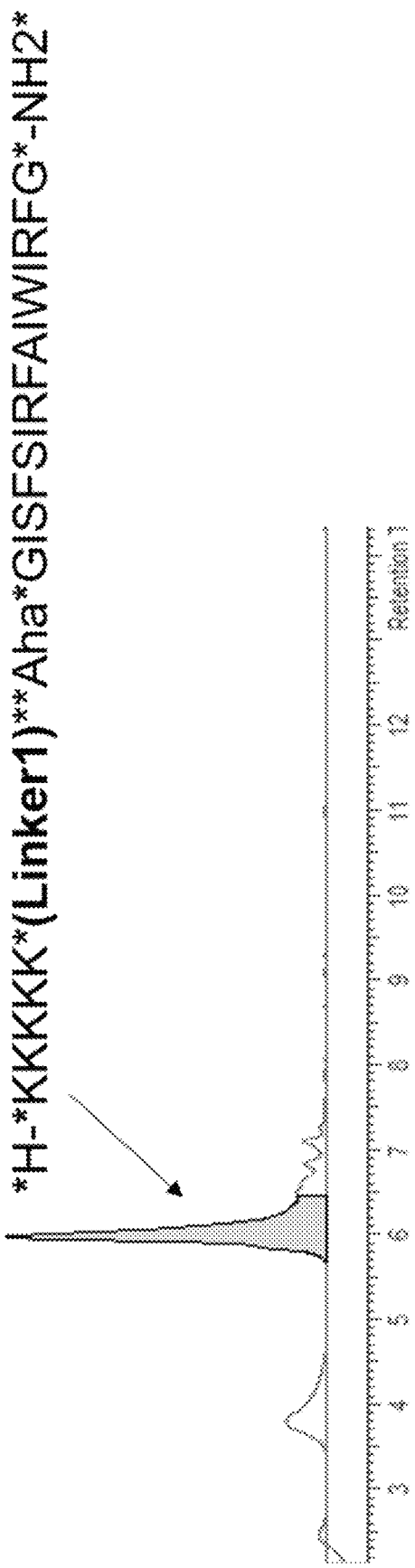

H-AhaGISFSIRFAIWIRFG-NH$_2$ (Aha=azidohomoalanine) (SEQ. ID. NO: 2) is an extremely hydrophobic peptide, which is insoluble in water, making the handling and HPLC purification after synthesis virtually impossible. In order to enhance solubility of this peptide a variant was prepared in which a cleavable N-terminal poly-lysine tag was synthesized after the peptide sequence and incorporated cleavable linker 1: H-KKKKK—(linker 1) AhaGISFSIRFAIWIRFG-NH$_2$ (10) (SEQ. ID. No: 3). Synthesis and purification of this modified peptide proceeded smoothly according to example 3 (FIG. 2B). Pure peptide 10 was dissolved in a 0.05 M aqueous NaHCO$_3$ solution and shaken for 2 h at r.t. (FIG. 2A). The cleavage reaction released the two peptides 11 and 12: While the poly-lysine tag 11 is water soluble, peptide 12 precipitated under the reaction conditions and could be easily isolated in high purity by centrifugation.

FIG. 2B: LC-MS of H-KKKKK (linker 1)-AhaGISFSIR-FAIWIRFG-NH$_2$ (10), MS (ESI): 545.4 [M+5H]$^{5+}$, 681.6 [M+4H]$^{4+}$, 908.3 [M+3H]$^{3+}$, 1362.0 [M+2H]$^{2+}$.

Figure 2C:
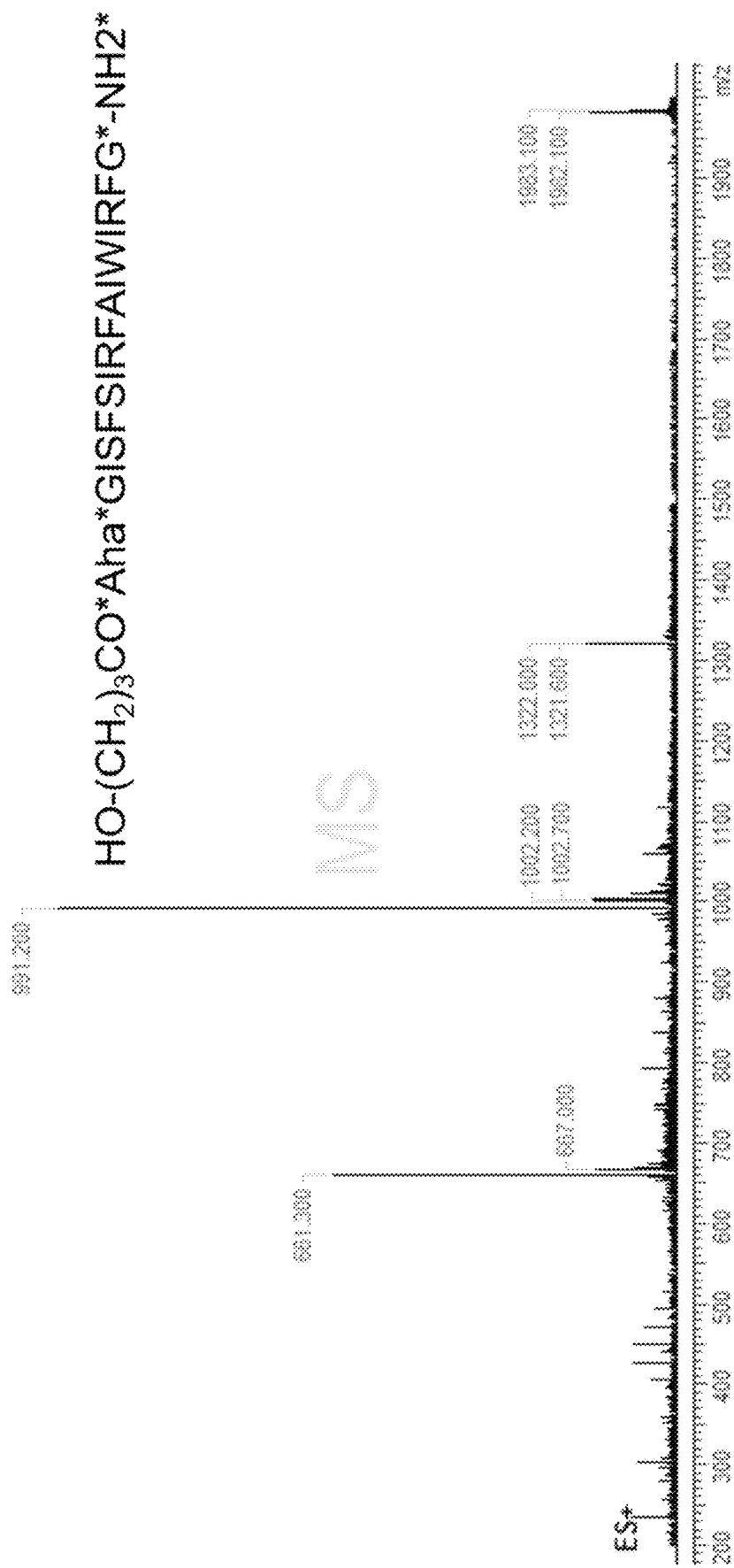

FIG. 2C: MS (ESI) of insoluble peptide 12 (MS (ESI): 661.5 [M+3H]$^{3+}$, 991.3 [M+2H]$^{2+}$, 1322.0 [3M+2H]$^{2+}$, 1983.1 [M+H]$^{+}$).

Example 5: Affinity Purification Via Biotin/Streptavidin Interaction

The introduction of N-terminal affinity labels in combination with a peptide synthesis method applying capping after each coupling step enables affinity purification of full-length products. The full-length peptide is captured on streptavidin coated magnetic beads, by-products (shorter sequences) are removed by filtration and the pure full-length peptide is released.

After SPPS of the target peptide, first linker 1, and then Fmoc-Glu(biotinyl-PEG)-OH were coupled to the N-terminus of the peptide. This resulted in H-GluBiotinylPEG-1-IIKKSTALL-NH$_2$ (13) (SEQ. ID. NO: 4). As the peptide sequence contains several sterically demanding amino acids, a complex mixture of full-length peptide and acetylated shorter fragments was obtained after cleavage from the resin. The crude product was dissolved in a phosphate buffer at pH=6.2 and incubated for 30 minutes with streptavidin coated magnetic beads. The supernatant was analyzed by LC-MS indicating the complete removal of the biotinylated peptide from the mixture. The by-product containing buffer solution was removed and the beads were washed several times with phosphate buffer (pH=6.2). Afterwards a volatile cleavage buffer (NH$_4$HCO$_3$, 0.02 M, pH=8.8) was added to the beads and after 30 min incubation the desired peptide 14 was released from the beads.

Scheme 5

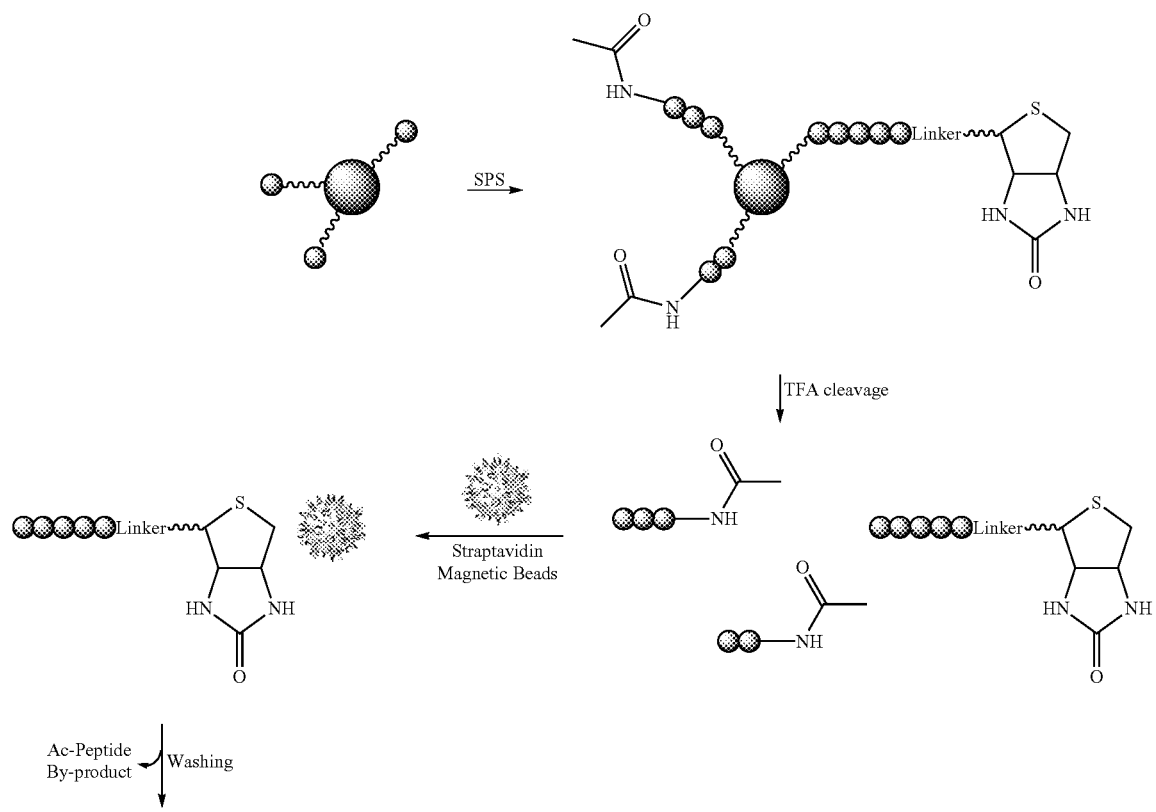

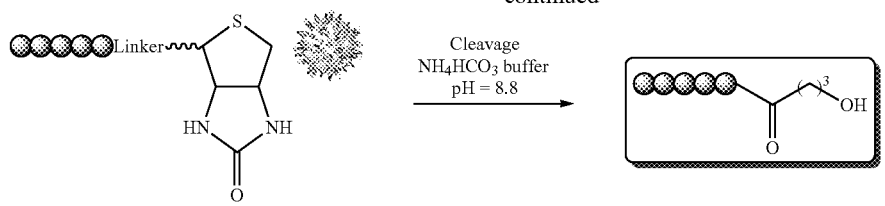

Figure 3A:
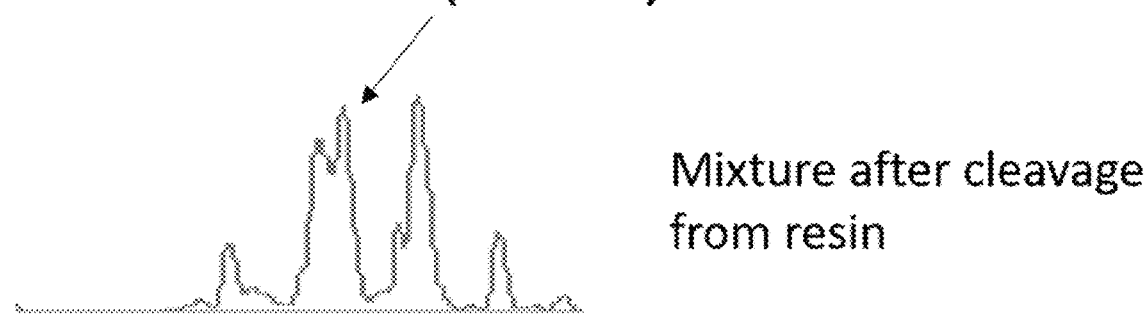
FIGS. 3A-3C depict affinity purification according to example 5 (SEQ ID NO: 4).
Figure 3B:
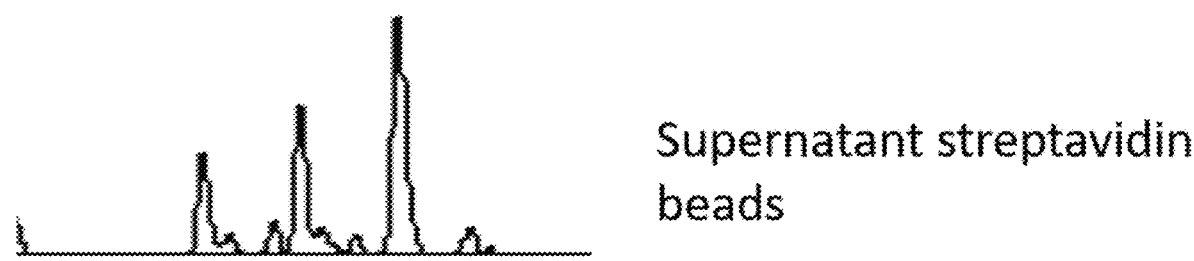
Figure 3C:
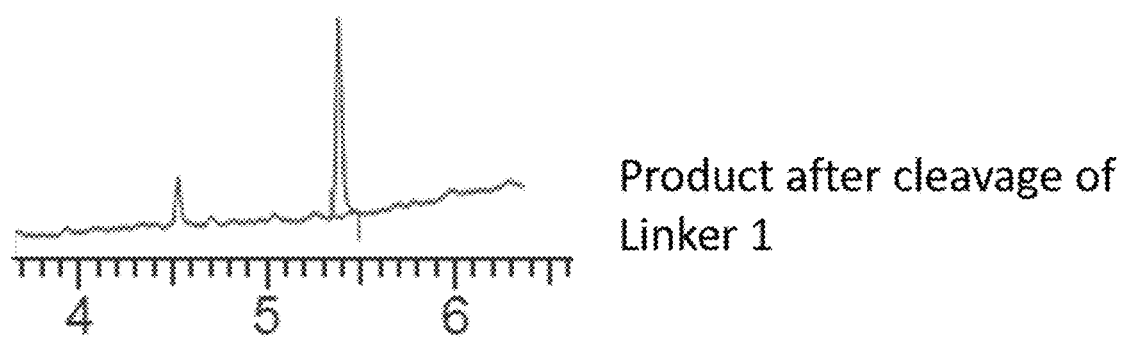

Results are shown in FIG. 3. FIG. 3A shows the crude peptide mixture obtained after SPPS and cleavage from resin. FIG. 3B shows the supernatant after 30 min incubation of the crude peptide mixture on streptavidin coated magnetic beads in phosphate buffer at pH=6.2. The N-terminally biotin tag containing peptide 13 is completely captured by streptavidin. c) After washing away the acetylated peptide by-products and incubating the magnetic streptavidin beads with NH$_4$HCO$_3$ at pH 8.8 for 30 min to release the desired peptide HO(CH$_2$)$_3$CO-IIKKSTALL-NH$_2$ (14) (SEQ. ID. NO: 4)

Example 6: Synthesis of DNA-peptide Conjugates Employing Cleavable Solubilizing

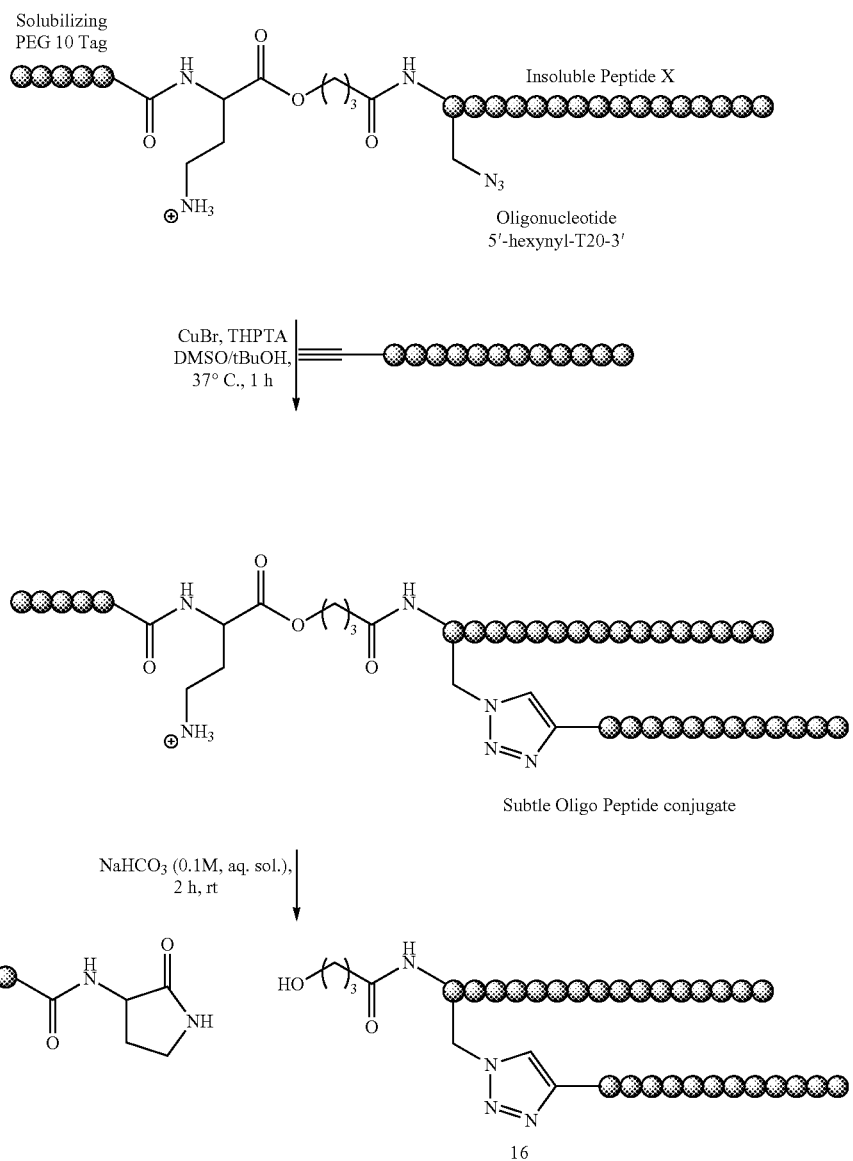

A peptide with the sequence H-PEG10 (linker 1) Aha AFDYLAQYHGG-NH$_2$ (15) (SEQ ID No: 5) was synthesized by SPPS (Aha=azidohomoalanine). Conjugation with the hexynyl-modified nucleic acid was performed by click chemistry. A solution of the azido-modified peptide 15 (4 mM in DMSO/tBuOH 3:1, 50 µl) was mixed with a solution of 5'-hexynyl-dT$_{20}$-3' (0.55 mM in H$_2$O, 180 µl) which was synthesized according to standard solid phase phosphoramidite approach. CuBr (100 mM in DMSO/tBuOH 3:1, 10 µl) and THPTA (100 mM in H$_2$O, 20 µl) were mixed separately and the preformed complex was added to the oligonucleotide-peptide solution. After 1 h shaking at 37° C. the click reaction was complete. Cleavage of the solubilizing PEG linker was obtained adding NaHCO$_3$ (0.1 M in H$_2$O, 3 ml). Dialysis of this solution (MWCO 1000 dialysis membrane) afforded the desired product 16.

5'-hex-T$_{20}$-3': MS (ESI): found 1544.3 $[M-4H]^{4-}$, calculated 1544.5 $[M-4H]^{4-}$.

Peptide X-5'-hex-T$_{20}$-3': MS (ESI): found 1647.7 $[M-5H]^{5-}$, calculated 1648.0 $[M-5H]^{5-}$.

Product 16: Peptide X-5'-hex-T$_{20}$-3'(Depegilated): MS (ESI): found 1525.6 $[M-5H]^{-5}$, calculated 1525.9 $[M-5H]^{-5}$.

Figure 4:
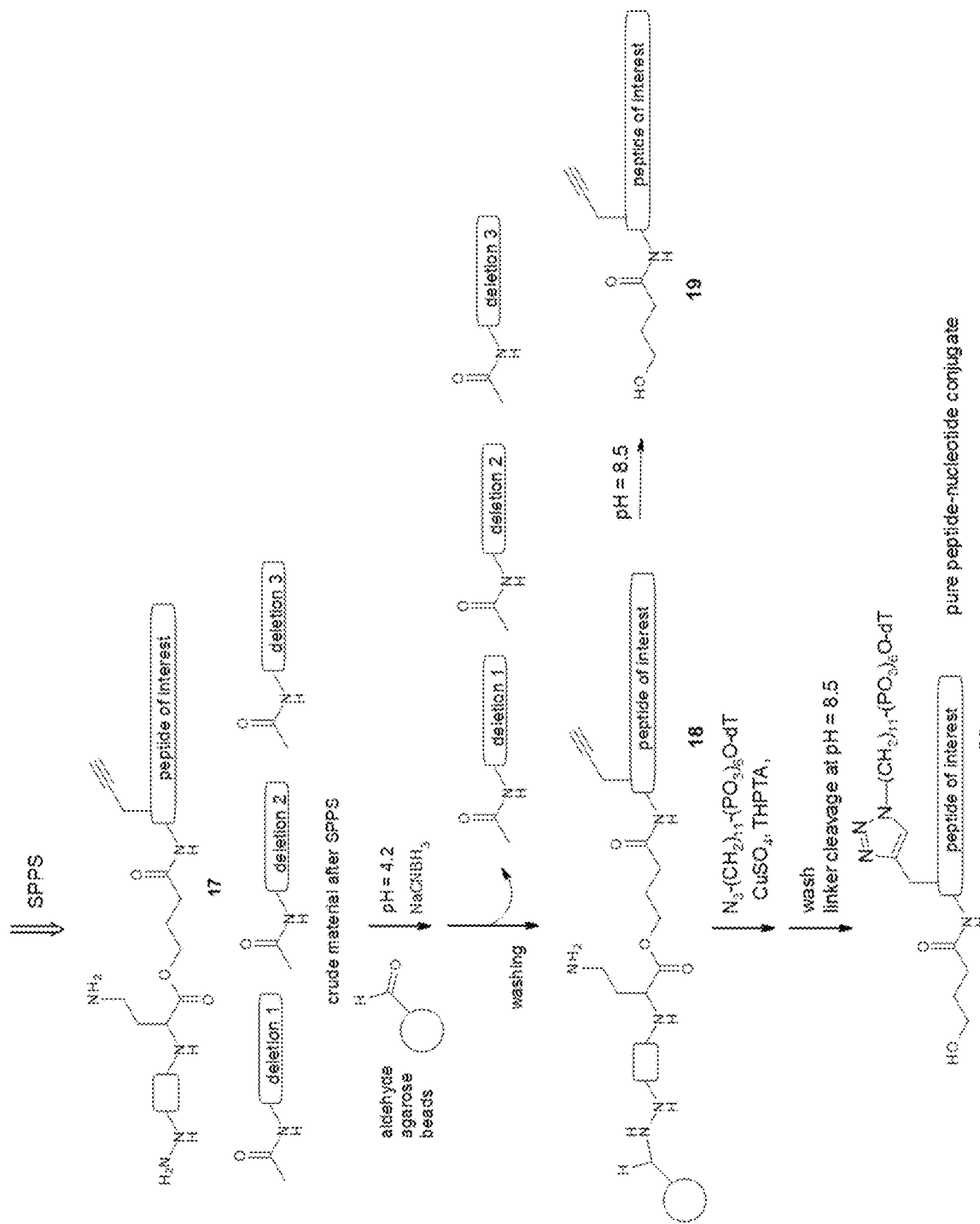
FIG. 4 sets forth a synthetic scheme, namely the rapid synthesis of nucleoside-peptide conjugates according to example 7. In particular, the FIG. 4 depicts the synthesis of peptides and nucleoside-peptide conjugates by solid-supported conjugation and non-chromatographic purification.

Example 7: Rapid Synthesis of Peptides and Nucleoside-Peptide Conjugates by Solid-Supported Conjugation and Non-Chromatographic Purification Using a Cleavable Immobilization Linker The reaction scheme disclosed in this example is illustrated in FIG. 4 and comprises two alternative routes A and B.

The peptide WWWWEAAAEAAAEAAAEAAAEAAAEAAAEAAAEAAAEAAAEAAAEAAAEAAAEEEE (SEQ. ID. No: 6) was synthesized on a rink-amide resin using automated Fmoc-SPPS. Next, Fmoc-Pra-OH (N-alpha-(9-Fluorenylmethyloxycarbonyl)-L-propargylglycine), Fmoc-protected cleavable linker 1, Fmoc-O2Oc-OH (8-(9-Fluorenylmethyloxycarbonyl-amino)-3,6-dioxaoctanoic acid) and Tri-Boc-hydrazine acetic acid were stepwise coupled to the resin-bound peptide by means of SPPS, yielding the desired peptide 17.

Figure 5A:
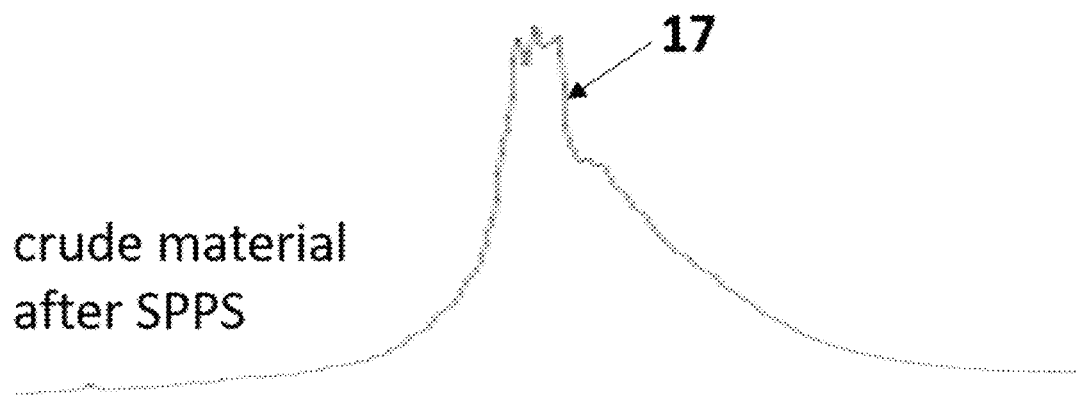
FIGS. 5A-5D set forth HPLC-analyses of conjugates obtained in example 7.
Figure 5B:
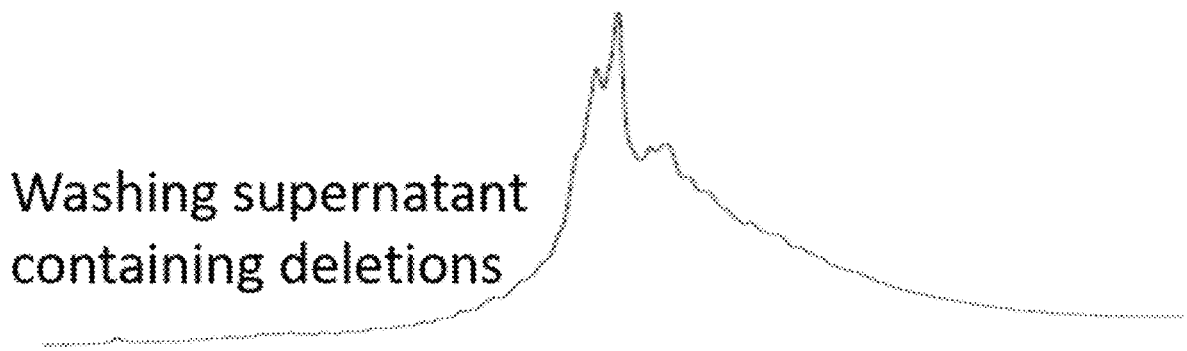
Figure 5C:
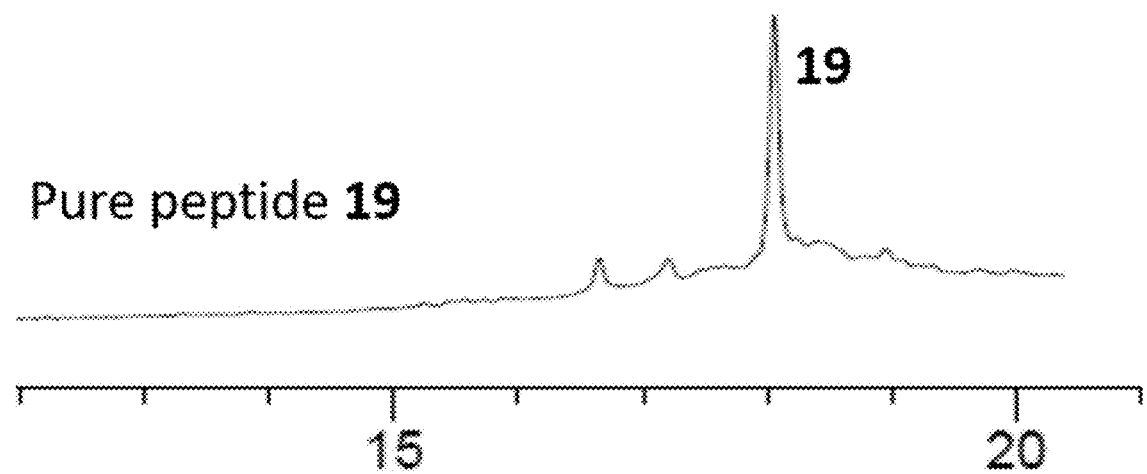
Figure 5D:
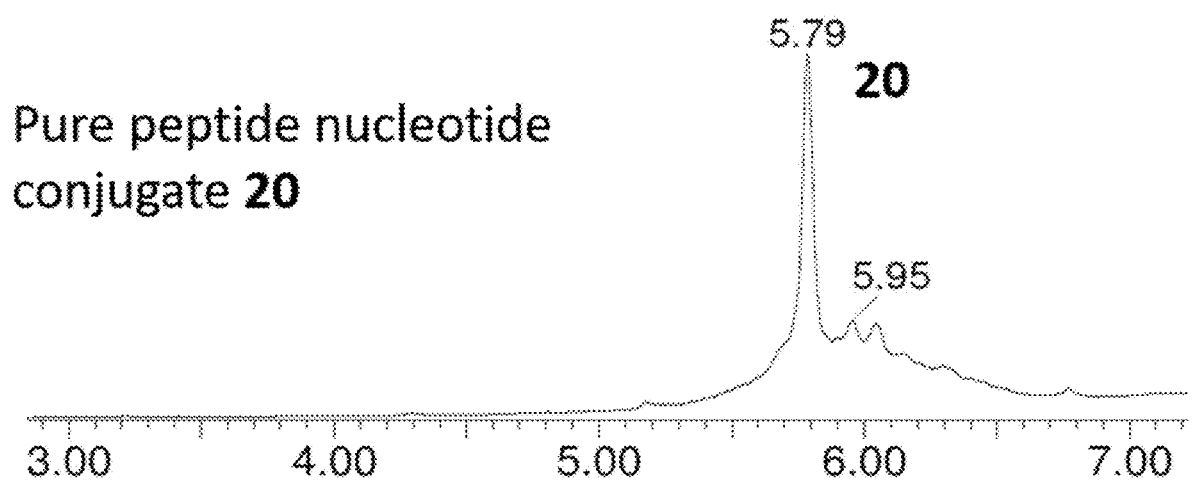

The peptide was cleaved from the resin with a mixture of TFA/TIS/H$_2$O (95/2.5/2.5). After 2 h the solution was concentrated and added to a solution of cold ether. The precipitated peptide was separated from the supernatant, dissolved in a mixture of H$_2$O/ACN (1/1) and freeze-dried. The crude material was dissolved in a mixture of an aqueous 0.25 M NaOAc/AcOH buffer (pH 4.2) and acetonitrile (20 vol. %). Sodium cyanoborohydride was added and the solution was transferred onto an aldehyde agarose resin. The suspension was agitated at room temperature and the progress of the immobilization reaction was monitored by HPLC (see FIGS. 5A and 5B). After immobilization (~1 h), the resin was washed with an aqueous 0.25 M NaOAc/AcOH buffer (pH 4.2), a mixture of H$_2$O/ACN (2/1) and water. The resin-bound propargylglycine-containing peptide 18 was brought into reaction with the azide-modified hexaphosphate thymidine (Fuller et al. PNAS 2016, 113 (19), p. 5233-4238) in presence of CuSO$_4$, THPTA, ascorbate and aminoguanidine in a mixture of aqueous 0.2 M NaH$_2$PO$_4$ buffer (pH 6.5) containing 20 vol. % DMSO (see FIG. 4, route A). The suspension was agitated at 37° C. for 16 h. The resin was washed with an aqueous 0.2 M NaHPO$_4$ buffer (pH 6.5) and a mixture of H$_2$O/ACN (2/1). The desired Nucleoside-peptide conjugate 20 was released in good purity by treatment of the resin with an aqueous 0.2 M Na$_2$HPO$_4$ buffer (pH 8.5) for 16 h at room temperature.

(HO(CH$_2$)$_3$CONH-Pra(N$_3$(CH$_2$)$_{11}$O(PO$_2$)$_6$dT) WWWW-EAAAEAAAEAAAEAAAEAAAEAAAEAAAEAAAE-AAAEAAAEAAAEAAAEEEE-NH$_2$:

MS (ESI): found 1101.3 $[M-6H]^{6-}$, calculated 1101.2 $[M-6H]^{6-}$; found 944.0 $[M-7H]^{7-}$, calculated 943.8 $[M-7H]^{7-}$.

Alternatively, the resin bound peptide 18 could be also released under mild basic conditions (0.2 M Na$_2$HPO$_4$ buffer, pH 8.5, r.t., 16 h) from the agarose resin (see FIG. 4, route B) even before the nucleoside-conjugation step. Under these conditions, the unmodified peptide 19

HO(CH$_2$)$_3$CONH-Pra WWWWEAAAEAAAEAAAE-AAAEAAAEAAAEAAAEAAAEAAAEAAAEAAAEA-AAEEEEE-NH$_2$ was isolated in high purity.

Product generation was monitored by HPLC analysis. FIG. 5 shows HPLC-analysis of the crude SPPS product (5A), the supernatant after immobilization (5B), the purified peptide 19 (5D) generated according to route B and the nucleoside-peptide conjugate 20 (5C).

Additional Embodiments

Additional Embodiment 1. A building block comprising the Structure

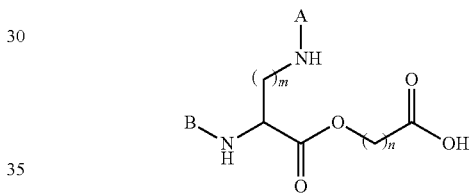

wherein 2≤n≤24, m=2 or 3,
A is an acid labile protective group and
B is a tag or base labile protective group.

Additional Embodiment 2. A building block according to additional embodiment 1, wherein A is Boc and/or B is Fmoc.

Additional Embodiment 3. A compound comprising the structure

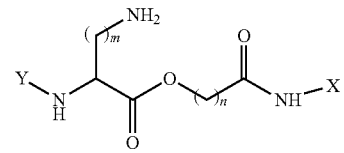

wherein
wherein 2≤n≤24, m=2 or 3,
X is a peptide, or a solid support and
Y is selected from a group consisting of a peptide, a functional group, a tag, and a peptide containing a functional group.

Additional Embodiment 4. A compound according to additional embodiment 3, wherein Y is either a solubility enhancing tag or an immobilization tag.

Additional Embodiment 5. A compound according to additional embodiment 4, wherein Y is selected from a group consisting of PEG, poly-lysine, poly-arginine, poly-glutamic acid, and poly-aspartic acid.

Additional Embodiment 6. A compound according to additional embodiment 4, wherein Y is selected from a group consisting of biotin, hydrazine, aminooxy, azide, alkynyl, alkenyl, aldehyde, pyrroloalanine, carboxy and thiol.

Additional Embodiment 7. A method comprising the steps of
a) synthesizing a peptide on a solid support, said peptide comprising a terminal amino group,
b) providing a building block according to any one of additional embodiments 1-2
c) coupling said building block to said peptide.

Additional Embodiment 8. The method of additional embodiment 7, further comprising the steps of
d) removing protective group B, and
e) coupling at least one amino acid building block to the terminal amino group.

Additional Embodiment 9. The method of additional embodiment 7, further comprising the steps of
d) removing protective group B,
e) optionally coupling at least one amino acid building block to the terminal amino group, and
f) coupling a tag or a functional group to the terminal amino group.

Additional Embodiment 10. The method of additional embodiment 9, wherein said functional group or tag is selected from a group consisting of PEG, poly-lysine, poly-arginine, poly-glutamic acid, poly-aspartic acid, biotin, hydrazine, aminooxy, azide, alkynyl, alkenyl, aldehyde, pyrroloalanine, carboxy and thiol.

Additional Embodiment 11. The method of any one of additional embodiments 7-10, further comprising the step of
g) removing protective group A at a pH≤6, thereby also removing other protective groups present on said peptide and cleaving said peptide from the solid support.

Additional Embodiment 12. The method of additional embodiment 11, further comprising the step of
d) cleaving the generated peptide at a pH≥8.

Additional Embodiment 13. The method of any one of additional embodiments 9-10, wherein said tag or functional group is a solubilizing tag, further comprising the steps of
g) removing protective group A at a pH≤6, thereby also removing other protective groups present on said peptide and cleaving said peptide from the solid support
h) purifying said peptide, and
i) cleaving off said solubilizing tag at a pH≥8.

Additional Embodiment 14. The method of any one of additional embodiments 9-10, wherein said tag or functional group is an immobilizing tag, further comprising the steps of
g) removing protective group A at a pH≤6, thereby also removing other protective groups present on said peptide and cleaving said peptide from the solid support
h) immobilizing said peptide via said immobilizing tag on a solid support
i) optionally conjugating said peptide to an additional chemical entity
j) cleaving off said immobilizing tag at a pH≥8.

Additional Embodiment 15. The method of additional embodiment 14, wherein said chemical entity is a nucleic acid, oligonucleotide or nucleotide, which is preferably a nucleoside-hexaphosphate.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

The invention claimed is:

1. A method comprising:
   a) synthesizing a peptide on a first solid support, said peptide comprising a first terminal amino group,
   b) providing a building block comprising the structure:

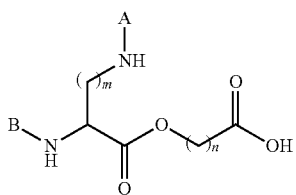

wherein $2 \leq n \leq 24$, m=2 or 3,
   A is an acid labile protective group, and
   B is a tag or base labile protective group; and
   c) coupling said building block to said first terminal amino group of said peptide.

2. The method of claim 1, wherein when B is a base labile protective group further comprising:
   c) removing the base labile protective group B from the building block to provide a deprotected amino group, and
   d) coupling at least one amino acid building block to the deprotected amino group of the building block, wherein the at least one amino acid building block comprises a second terminal amino group.

3. The method of claim 1, wherein when B is a base labile protective group further comprising:
   c) removing the base labile protective group B from the building block to provide a deprotected amino group,
   e) optionally coupling at least one amino acid building block to the deprotected amino group of the building block, wherein the at least one amino acid building block comprises a second terminal amino group, and
   e) coupling a tag or a functional group to either (i) the second terminal amino group of the at least one amino acid building block, or (ii) the deprotected amino group of the building block.

4. The method of claim 3, wherein said tag or functional group is selected from the group consisting of PEG, poly-lysine, poly-arginine, poly-glutamic acid, poly-aspartic acid, biotin, hydrazine, aminooxy, azide, alkynyl, alkenyl, aldehyde, pyrroloalanine, carboxy, and thiol.

5. The method of claim 1, further comprising:
   removing the acid labile protective group A from the building block at a pH≤6, thereby also removing other protective groups present on said peptide and cleaving said peptide from the first solid support.

6. The method of claim 5, further comprising:
   contacting said cleaved peptide with a buffer having a pH≥8.

7. The method of claim 3, wherein said tag or functional group is a solubilizing tag, and wherein the method further comprises:
   g) removing the acid labile protective group A from the building block at a pH≤6, thereby also removing other protective groups present on said peptide and cleaving said peptide from the first solid support,
   h) purifying said cleaved peptide, and
   i) cleaving said solubilizing tag at a pH≥8.

8. The method of claim 3, wherein said tag or functional group is an immobilizing tag, and wherein said method further comprises:
   g) removing the acid labile protective group A from the building block at a pH≤6, thereby also removing other protective groups present on said peptide and cleaving said peptide from the first solid support,
   h) immobilizing said cleaved peptide via said immobilizing tag on a second solid support,
   i) optionally conjugating said cleaved peptide to an additional chemical entity, and
   j) cleaving said immobilizing tag at a pH≥8.

9. The method of claim 8, wherein said additional chemical entity is selected from the group consisting of a nucleic acid, an oligonucleotide, and a nucleotide.

10. The method of claim 9, wherein said nucleotide is a nucleoside-hexaphosphate.

* * * * *